US008273817B2

(12) United States Patent
Gustafson et al.

(10) Patent No.: US 8,273,817 B2
(45) Date of Patent: Sep. 25, 2012

(54) CLAYLINKED POLYMER GELS IN NEW PHYSICAL FORMS, METHODS FOR THEIR FORMATION AND USES THEREOF

(75) Inventors: Ingrid Gustafson, Åsa (SE); Anna Körner, Göteborg (SE); Shabira Abbas, Göteborg (SE); Maria Fanto, Lindome (SE); Rozalia Bitis, Kungsbacka (SE); Charlotta Hanson, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 272 days.

(21) Appl. No.: 12/680,070

(22) PCT Filed: Sep. 25, 2008

(86) PCT No.: PCT/SE2008/051074
§ 371 (c)(1),
(2), (4) Date: Mar. 25, 2010

(87) PCT Pub. No.: WO2009/041903
PCT Pub. Date: Apr. 2, 2009

(65) Prior Publication Data
US 2010/0210746 A1    Aug. 19, 2010

(30) Foreign Application Priority Data

Sep. 27, 2007   (WO) .................. PCT/SE2007/050680

(51) Int. Cl.
*C08J 9/35*     (2006.01)
*C08F 292/00*   (2006.01)
*B01J 20/26*    (2006.01)

(52) U.S. Cl. ........ 524/445; 524/446; 524/916; 521/142; 521/147; 521/149; 521/189; 523/205

(58) Field of Classification Search ................ 524/445, 524/446, 916; 523/205; 521/142, 147, 149, 521/189
See application file for complete search history.

(56) References Cited

U.S. PATENT DOCUMENTS

| | | | |
|---|---|---|---|
| 6,159,591 A | 12/2000 | Beihoffer et al. | |
| 6,534,239 B2 | 3/2003 | Varanasi et al. | |
| 7,993,892 B2 * | 8/2011 | Takada et al. | ................. 435/176 |
| 2001/0049413 A1 | 12/2001 | Haraguchi | |
| 2005/0234179 A1 * | 10/2005 | Haraguchi et al. | ............ 524/445 |
| 2005/0239942 A1 | 10/2005 | Herfert et al. | |
| 2005/0245393 A1 | 11/2005 | Herfert et al. | |
| 2007/0148432 A1 | 6/2007 | Baker et al. | |

FOREIGN PATENT DOCUMENTS

| | | |
|---|---|---|
| CA | 2 381 910 A1 | 2/2001 |
| EP | 1 160 286 A1 | 12/2001 |
| EP | 1 829 896 A1 | 9/2007 |
| WO | WO 00/72958 A1 | 12/2000 |
| WO | WO2006064810 * | 6/2006 |

OTHER PUBLICATIONS

International Search Report for PCT/SE2008/051074 completed Dec. 22, 2008.
Written Opinion for PCT/SE2008/051074 completed Dec. 22, 2008.
Junping Zhang et al., "Study on superabsorbent composites. IX: Synthesis, characterization and swelling behaviors of polyacrylamide/clay composites based on various clays", Reactive & Functional Polymers 67, 2007, pp. 737-745.
Ji Zhang et al., "Preparation and properties of polyacrylate/bentonite superabsorbent hybrid via intercalated polymerization", Materials Letters 61, 2007, pp. 316-320.
An Li et al., Preparation of Starch-*Graft*-Poly(Acrylamide)/Attapulgite Superabsorbent Composite, Journal of Applied Polymer Science, vol. 98, 2005, pp. 1351-1357.
Meifang Zhu et al., "A Novel Highly Resilient Nanocomposite Hydrogel with Low Hysteresis and Ultrahigh Elongation", Macromolecular Rapid Communications, 2006, 27, pp. 1023-1028.
Zhang Weian et al., "Synthesis and properties of a novel hydrogel nanocomposites", Materials Letter 59, 2005, pp. 2876-2880.
Kazutoshi Haraguchi et al., "Mechanism of Forming Organic/Inorganic Network Structures during In-situ Free-Radical Polymerization in PNIPA-Clay Nanocomposite Hydrogels", Macromolecules, 2005, 38, pp. 3482-3490.
Myriam Silberberg-Borhnik et al., Osmotic Deswelling of Weakly Charged Poly(Acrylic Acid) Solutions and Gels., Journal of Polymer Science: Part B: Polymer Phusics, 1995, vol. 33, pp. 2269-2279.
Volkan Can et al., "Shake gels based on Laponite-PEO mixtures: effect of polymer molecular weight", Designed Monomers and Polymers, 2005, vol. 8, No. 5, pp. 453-462.
Oguz Okay et al., "Polyacrylamide-Clay Nanocomposite Hydrogels: Rheological and Light Scattering Characterization", Macromolecules, 2007, 40, pp. 3378-3387.
A. Leon et al., The synthesis and characterization of monodisperse poly(acrylic acid) and poly(methacrylic acid), Colloid Polym Sci 272, pp. 427-432, 1994.
Dawid Stawski et al., "Polymerization of itaconic acid", Polimery 2005, 50, pp. 118-122.
J. De Groot et al., "Dissociation Behavior of Poly(maleic acid): Potentimetric Titrations, Viscometry, Pulsed Field Gradient NMR, and Model Calculations", Macromolecules 1998, 31, pp. 4182-4188.
G. Smets et al., "Hydrolysis of Polyacrylamide and Acrylic Acid-Acrylamide Copolymers", Journal of Polymer Science, vol. XL, pp. 217-226, 1959.
Wei Zhang et al., "Surprising Conversion of Nanocomposite Hydrogels with High Mechanical Strength by Posttreatment: From a Low Swelling Ratio to an Ultrahigh Swelling Ratio", Journal of Polymer Science: Part A: Polymer Chenistry, vol. 44, pp. 6640-6645, 2006.
Jovan Velickovic, et al., The synthesis and characterization of poly(itaconic) acid, Polymer Bulletin 32, pp. 169-172, 1994.

* cited by examiner

*Primary Examiner* — Irina S Zemel
(74) *Attorney, Agent, or Firm* — Buchanan Ingersoll & Rooney PC

(57) ABSTRACT

A fiber, film or foam includes a plasticizer and a charged claylinked gel (A). The charged claylinked gel (A) includes clay nanoparticles (C) which are crosslinked by a charged polymer (A') such that any particular clay nanoparticle is linked to at least one other clay nanoparticle by the charged polymer (A'). Methods for producing the fibers, film and foam are also provided.

20 Claims, 6 Drawing Sheets

CLAYLINKED POLYMER GELS IN NEW PHYSICAL FORMS, METHODS FOR THEIR FORMATION AND USES THEREOF

TECHNICAL FIELD

The present invention relates to a new claylinked gel in new physical forms, together with methods for their formation and uses thereof.

BACKGROUND OF THE INVENTION

Advances in absorbent article technology have stimulated the search for absorbent (often superabsorbent) materials with desirable properties such as high absorption, high gel strength and low health risks to wearers. Gels comprising clay nanoparticles and polymer have been identified as a new class of absorbent materials which are suitable for such applications. The clay nanoparticles link the polymer structure, providing strong and elastic materials which can thus contain less (or even no) organic bulk cross-linker which make the gel brittle.

One way to incorporate clay nanoparticles into polymer gels is by adding the clay nanoparticles into a traditional polymerization reaction comprising initiator, a high concentration of bulk cross-linker and monomer(s). In such a material, the nanoparticles are not deliberately bonded to the polymer via chemical bonds, but rather physically trapped in its three-dimensional networked structure. Such materials are not considered "claylinked" within the meaning of the present invention.

An example of this type of material is provided in WO 00/72958, which describes an "MCX" mixture comprising monomer, clay particles, cross-linking agent and mixing fluid. The MCX mixture is polymerized upon exposure to a polymerization initiator and a networked polymer/clay alloy is formed. The clay particles are not strongly bonded to the polymer chains in such materials, but are rather embedded in the polymer matrix. That is, they do not function as cross-linkers. If insufficient organic cross-linking is present, therefore, the clay may separate from the polymer, which can cause problems for the integrity and properties of the material and undesired release of clay nanoparticles.

Similarly, CA 2 381 910 describes water-absorbing polymers having interstitial compounds. The clay (zeolite) is not part of the structure as a cross-linker. The zeolite acts to absorb odour.

An alternative way to incorporate clay nanoparticles into polymer gels is by the formation of cross-linked materials comprising nanoparticles which are crosslinked by polymer, so-called "claylinked gels". An appropriate monomer is added to an exfoliated dispersion of clay nanoparticles, then polymerised with the appropriate initiator system, forming links between the nanoparticles. A three-dimensional network of clay nanoparticles and polymer is formed, in which any particular clay nanoparticle is linked to at least one other clay nanoparticle by polymer. Such materials are stronger than those in which clay nanoparticles are simply embedded in the polymer network, as the clay nanoparticles are chemically bonded to the polymer. For this reason, leakage of clay nanoparticles from such materials is also minimised.

For example, EP 1 160 286 discloses an organic/inorganic hybrid hydrogel based on polyacrylamides.

Another example is found in Zhu et al., *Macromol. Rapid Communications*, 2006, 27, 1023-1028, which describes a nanocomposite (NC) gel based on clay-linked polyacrylamide. High tensile strength is obtained.

To date, neutral (uncharged) polymers such as polyacrylamides have been used in the formation of claylinked gels (see EP 1 160 286 and other documents cited above). The reason for this is the difficulties encountered when introducing charged species to an exfoliated dispersion of clay nanoparticles, as will now be explained.

At the nano-scale, forces between nanoparticles such as e.g. static charges or van der Waal's forces become significant, meaning that the behaviour of nanoparticles is often rather different to that of larger particles. Nanoparticular clays often have a surface charge distribution which varies significantly over a small distance. For example, exfoliated laponite is a synthetic, disc-shaped silicate, with a thickness of approximately 1 nm and a diameter of 25 nm. In aqueous dispersions, laponite has a strongly negative charge on its faces and a weakly localized positive charge on its edges. The surface charges on such nanoparticles cause the formation of electrical double layers e.g. of $Na^+$ ions in aqueous solution. The electrical double layers which are formed around each clay nanoparticle (or in certain regions of each nanoparticle) cause the nanoparticles to repel each other in aqueous solution, thus providing dispersions of non-interacting particles which are generally transparent or translucent and which have low viscosity.

Addition of charged water-soluble compounds to dispersions of clay nanoparticles reduces the osmotic pressure holding the $Na^+$ ions away from the nanoparticle surface, so that the electrical double layer becomes thinner. The nanoparticles can therefore come closer to one another, which results in their agglomeration. Agglomeration is clearly observable by eye, as low concentration dispersions of clay nanoparticles are initially transparent but become cloudy and form a precipitate upon the addition of a charged compound. High concentration dispersions of clay nanoparticles form gel-like agglomerates upon the addition of charged water-soluble compounds.

Weian et al., *Materials Letters*, 2005, 59, 2876-2880 describe how montmorillonite can be stabilised using a reactive intercalating agent, followed by addition of acrylic acid and polymerization thereof.

Haraguchi et al., *Macromolecules*, 2005, 38, 3482-3490 discusses the mechanism of forming nanocomposite gels based on poly(N-isopropylacrylamide). Silberberg-Bouhnik et al. *J. Polym. Sci. B, Polym. Phys.* 1995, 33, 2269-2279 discusses the dependence of the swelling ratio of a polyacrylic acid gel (without clay particles) upon its degree of ionisation. V. Can and O. Okay Designed monomers and polymers, vol. 8, no. 5, 453-462, (2005) describes the formation of physical gels between polyethylene oxide (PEO) chains and laponite particles.

Claylinked gels comprising neutral polymers, such as polyacrylamide, are known, as discussed above. Charged polymers (e.g. polyacrylate polymers) have higher water-absorption capacity. This may be due to repulsion between near-lying charged groups within the polymer, which allows greater expansion. Additionally, osmotic pressure builds up between the inside and outside of the charged gels when exposed to water, which drives the absorption process. It would therefore be desirable if claylinked gels could be synthesised which comprised charged polymers.

However, addition of charged monomers to a dispersion of clay nanoparticles causes agglomeration of the nanoparticles, as discussed above, so claylinked gels comprising charged polymers cannot be synthesized using the methods described for neutral polymers such as polyacrylamide.

The present invention provides specific forms of claylinked gels comprising charged polymers, and a method for producing them which overcome the problems associated with known synthesis routes. In this way, claylinked gels comprising charged polymers can be obtained which could not be produced previously.

A superabsorbent material in the form of a foam or a fibrous network has the advantage that it absorbs liquid not only in the material itself (the walls of the pores, or the fibre structure), but also in the pores of the foam, or the interstices between the fibres. However, foam and fibrous materials made of traditional superabsorbent polymers (e.g. polyacrylic acid/polyacrylate polymers) are usually hard and stiff when dry, not elastic enough and brittle when wet—they tend to fall apart under pressure. For these reasons, superabsorbent materials are usually included in absorbent articles in granular form.

It would therefore be advantageous to design a superabsorbent material which could exist in a form which is soft and elastic, and which maintains its elastic properties in both dry and wet states.

SUMMARY OF THE INVENTION

Thus, the invention provides a fibre, film or foam comprising:
a. a plasticizer and
b. a charged claylinked gel (A), said charged claylinked gel (A) comprising clay nanoparticles (C) which are crosslinked by a charged polymer (A') such that any particular clay nanoparticle is linked to at least one other clay nanoparticle by said charged polymer (A').

Using claylinked superabsorbent foams, films and fibres provides materials which are superior to conventional crosslinked superabsorbent foams, fibres and films, as they are elastic and strong in wet conditions and by combining them with a plasticiser they are also strong and elastic in dry conditions.

The charged polymer (A') is suitably polyacrylate or polyacrylsulfonate. The polyacrylate suitably comprises pendant carboxylate —$(CO_2^-)$ and/or pendant carboxylic acid groups —$(CO_2H)$ and the polyacrylsulfonate suitably comprises pendant sulfonate —$(SO_3^-)$ and/or pendant sulfonic acid groups —$(SO_3H)$.

The clay nanoparticles (C) may be selected from the group consisting of: montmorillonite, saponite, nontronite, laponite, beidellite, iron-saponite, hectorite, fluorohectorite, sauconite, stevensite, magdite, vermiculite, kaolin minerals (including kaolinite, dickite and nacrite), mica minerals (including illite), chlorite minerals, palygorskite and combinations thereof, preferably montmorillonite, laponite and hectorite. The clay nanoparticles (C) may have an average particle diameter of 5-500 nm, preferably 5-100 nm, more preferably 5-50 nm. Suitably, the charged polymer (A') comprises a low amount of organic bulk cross-linker (e.g. less than 1 mol %, more preferably less than 0.5 mol % based on the amount of monomer).

The invention particularly relates to a foam as described herein. The foam may have a pore size gradient from one region thereof to another. The foam according to the invention may additionally comprise a viscosity control agent.

A method for making the foam material is also provided, comprising the steps of:
a. providing an partly or fully exfoliated dispersion of clay nanoparticles (C) in water;
b. adding one or more monomers which comprise neutral functional groups (B1),
c. adding a plasticizer,
d. optionally, adding a viscosity control agent and/or surfactant,
e adding a polymerization initiator,
f. foaming the mixture of clay nanoparticles (C), plasticizer and neutral monomers (B1),
g. polymerising the neutral monomers (B1) to form a neutral claylinked foam,
h. hydrolysing the neutral functional groups (B1) to charged functional groups (A1) wherein steps a., b., c. d. and e. can take place in any order.

The foaming step preferably takes place by means of a blowing agent, but may take place by means of any of the methods described below.

The invention also relates to a fibre as described herein. A method for making the fibre is also provided, comprising the steps of:
a. providing an partly or fully exfoliated dispersion of clay nanoparticles (C) in water;
b. adding one or more monomers which comprise neutral functional groups (B1),
c. adding a plasticizer,
d. adding a polymerization initiator,
e. polymerising the monomer to form a neutral claylinked gel (B),
f. spinning the charged claylinked gel (A) into a fibre
g. hydrolysing the neutral functional groups (B1) to charged functional groups (A1), thus forming a charged claylinked gel (A),
wherein steps a., b. c. and d. and steps f. and g. can independently take place in any order.

The invention also relates to a film as described herein, and a method for making thereof. The method for making the film, comprises the steps of:
a. providing an partly or fully exfoliated dispersion of clay nanoparticles (C) in water;
b. adding one or more monomers which comprise neutral functional groups (B1),
c. adding a plasticizer,
d. adding a polymerization initiator,
e. polymerising the neutral monomers (B1) to form a neutral claylinked gel,
f. forming the neutral claylinked gel into a film,
g. hydrolysing the neutral functional groups (B1) to charged functional groups (A1)
wherein steps a., b., c. and d. and steps f. and g. can take place in any order.

The invention also relates to the use of a foam, film or fibre as described herein in an absorbent article, and an absorbent article comprising the foam, film or fibre.

DEFINITIONS

A "charged" polymer according to the invention is one which comprises one or more charged functional groups (A1), such as at least 2 mol %, at least 10 mol % or at least 20 mol % of charged functional groups, which provide the polymer with an overall positive or negative charge. The polymer may be negatively-charged, in which case it may incorporate negatively-charged functional groups (A1) such as —$CO_2^-$, —$SO_3^-$, —$O^-$, —$S^-$, —$PO_3^-$ and derivatives thereof. The polymer may alternatively be positively-charged, in which case it may incorporate positively-charged functional groups (A1) such as polymers containing charged amine functional groups and derivatives thereof. Counterions to the charged functional groups may be any counterion commonly known in the art.

A "neutral" polymer according to the invention is one which does not comprise charged functional groups (A1), but only neutral functional groups (B1).

As used herein, the term "polyacrylate" is used to refer to a polymer which—at least in regions thereof—has a hydrocarbon backbone with pendant carboxylic acid and/or carboxylate groups.

As used herein, the term "polyacrylamide" is used to refer to a polymer which—at least in regions thereof—has a hydrocarbon backbone with pendant amide groups.

The term "crosslinked" is used herein to describe a material in which regions of a first component of the material are interlinked by means of a second component. Generally, covalent bonds are formed between the first and second components. Increased crosslinking in a material provides it with increased strength and increased stiffness (lower flexibility).

The term "claylinked gel" is used to describe a material in which clay particles are interlinked by a polymer. Chemical bonds (e.g. ionic, covalent or hydrogen bonds, or complex formation) are formed between the clay particles and the polymer, or an initiator molecule, so that the materials are linked at the molecular level rather than just being associated with each other. This is in contrast to the clay particles simply being dispersed or embedded in the polymer. As such, a three-dimensional network of clay particles and polymer is provided, in which any particular clay nanoparticle is linked to at least one other clay nanoparticle by polymer. The structure of claylinked materials may equally be considered as polymer being interlinked by clay particles.

"Nanoparticles" are particles with dimensions in the nanoscale. For instance, average diameters of nanoparticles according to the present invention lie between 1 and 500 nm. Nanoparticles often have a maximum diameter of 100 nm. At such small dimensions, forces between particles such as e.g. static charges or van der Waal's forces become significant, meaning that the behaviour of nanoparticles is often rather different to that of larger particles.

The term "exfoliated" means that the nanoparticles are dispersed predominantly in an individual state through out the carrier material, which could be a solvent or a polymer hydrogel.

DETAILED DESCRIPTION OF PREFERRED EMBODIMENTS

Figure 1:
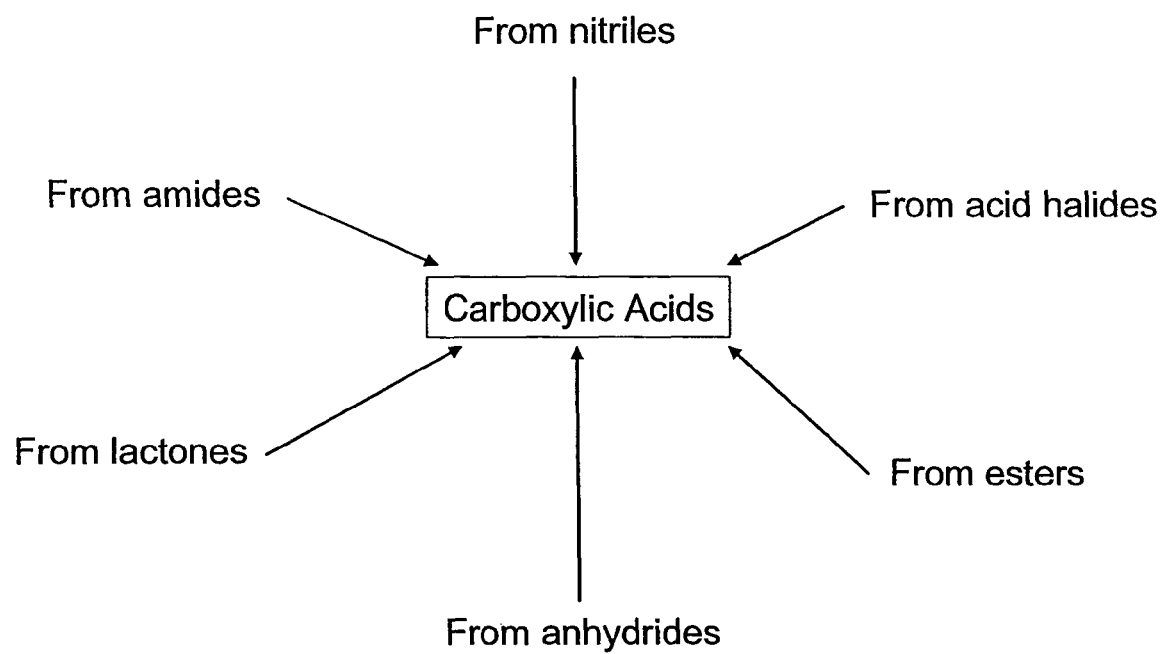
FIG. 1 is an illustration of synthesis routes for making carboxylic acid functionalities.

The present invention provides a fibre, film or foam of a certain material. The fibre, film or foam comprises to main components: a plasticizer, and a charged claylinked gel (A). The fibre, film or foam of the invention may consist solely of these two components, or may comprise further components.

Foams are materials that are formed by trapping gas bubbles in a liquid or solid. Solid foams form an important class of lightweight cellular materials. Foams can be classified into two types of cellular materials based on their pore structure. The first type of foam is called "open-cell foam" which contains pores that are connected to each other. The second type of foam is called "closed-cell foam" and does not have an interconnected pore structure. Claylinked foams have good elastic properties. These elastic foams provide good liquid storage capacity and good liquid distribution. By the fact that the foam contains open cells which are made of elastic cell walls the mechanical properties of the foam are further improved, which means that the structure is deformable when it is submitted to mechanical stresses, and it will thus resume its original shape when the load is removed, compared with a foam with non-elastic cell walls or much less elastic cell walls. Elastic cell walls of a foam can make it possible for the foam structure to expand when liquid enters the cell and shrink when the liquid is drained. Elastic foams are also better at withstanding both tensile and shearing stresses. Claylinked foam constituting the absorbent core in an absorbent article is thus more flexible and pliable than a structure that is mainly based on cellulosic fibers and SAP particles. In addition, elastic foams are more easily compressed, i e they can be compressed to higher densities and yet expand when wetted. Therefore, it is possible to compress the product in its packaged state, without it being damaged due to its brittleness.

Solid foams can be prepared by various methods but the process is divided into two main steps; 1. Bubble initiation and growth and 2. Solidifying process, respectively 1. Bubble Initiation and Growth There are several ways available e.g.

a. Whipping gas into a liquid b. Injecting gas into a liquid c. Bubbles can also form spontaneously in a liquid when the vapour pressure of the gas becomes higher than the ambient pressure d. Nucleation of gas bubbles by either chemical methods or physical methods e. A two phase system could also be achieved in a solid/liquid system. The solid phase will then be removed after the solidifying process Chemical methods are often associated with using blowing agents or porogens. Blowing agents are additives which are able to evolve gas through well-defined chemical reactions and produce foam structure in polymeric materials. Blowing agents include compressed gases that expand when pressure is released, soluble solids that leave pores when leached out, liquids that develop cells when they change to gases, and chemical agents that decompose or react under the influence of heat to form a gas. Chemical blowing agents range from simple salts such as ammonium or sodium bicarbonate to complex nitrogen releasing agents. Although the terms "blowing agents" and "porogens" are often used to mean the same thing, porogens are sometimes defined as those blowing agents which do not decompose through well-defined chemical reactions, but that, at very high temperatures, fall randomly apart in all kinds of molecular fragments. Examples of blowing agents/porogens are sodium bicarbonates and ammonium bicarbonates which produce carbon dioxide gas when submitted to acidic conditions. Other examples are isocyanate-groups which produce carbon dioxide when submitted to water or azo-groups which produce nitrogen gas when submitted to heat.

Bubbles could also be produced by emulsions and microemulsions which include changing physical conditions to ensure a cellular structure. Examples are making emulsions or microemulsions with hydrocarbons with a low vaporization temperature (for instance heptane or acetone). Another example is producing a foam-structure using water and vaporizing the water using a freeze drying process. Supercritical fluids, like supercritical carbon dioxide could also be used to produce a cellular structure In the bubble initiation and growth phase there are several components that could be used to facilitate this process. Examples are surface active components, so called surfactants. Some particulates or fibres could also be used. Also some proteins could be used as surface active materials. The cellular structure could also be stabilized using a viscosity control agent in the liquid phase, or in the air-liquid interface.

2. Solidifying Process

A solid foam is produced in the solidifying process which often is a polymerization of monomers in the liquid phase. The polymerization could be by a radical mechanism. Step-growth polymerization is also plausible. The polymerization temperature could be ambient or over or below room-temperature. Polymerization which takes place in a two phase system, in which water, at temperatures below the freezing point, is one of the phases produces so-called cryogels. When water is removed, a foam is produced It is also plausible that the solidifying process could occur by a physical change of the liquid phase for instance gelation and/or drying.

By controlling the nature of the bubble initiation and growth process it is possible to produces cellular structures with different pore sizes, pore structures and/or pore gradients. In one embodiment, therefore, the foam has a pore size gradient from one region thereof to another. The foam can therefore comprise different pore sizes and pore gradients in different regions thereof. The pore gradient can be in the z-direction (from the upper part of the absorption structure down to the lower portion of the absorption structure) with largest pores in the upper part leading to smaller and smaller pores as the lower portion is reached. One advantage of such a structure is that the upper part of the absorbent structure located closest to the wearer is provided with a higher liquid distributing capacity than the lower liquid storage portion of the absorbent structure. Furthermore, the lower part of the foam has a higher capillary pressure and thereby empties the upper part, allowing further wetting and giving a dry upper surface.

In order to obtain such a gradient, different layers of foam are manufactured and placed on top of each other. By applying the different layers on top of each other before they are dry, an integrated structure will be obtained, where the layers partly penetrate into each other. One advantage of such an integrated structure as compared to an absorbent structure consisting of separate layers is that a subsequent joining step is eliminated. Such a structure is thus cheaper to manufacture since the need for an adhesive and/or energy supply for joining the layers is eliminated. Another advantage with an integrated structure is that the function of the structure is improved in such a way that the liquid transport does not risk to be deteriorated at the transition from a first layer to a second layer due to insufficient contact between the layers.

Suitably, the pore walls of the foam in the liquid acquisition portion can be more claylinked, i.e. contain more nanoparticles than the pore walls of the liquid storage portion. A very highly claylinked material can not absorb so much liquid as a material having a lower degree of claylinking. A material with a high degree of claylinking i.e. containing more nanoparticles, has a lower risk of gelblocking. An absorbent structure according to this embodiment can be formed by preparing two or more foam layers, in which a higher amount of nanoparticles is added to the polymer solution which is going to form the liquid acquisition portion and a smaller amount of nanoparticles is added to the polymer solution that is going to form liquid storage portion. After foaming and solidifying, but before drying, the different layers are placed on top of each other, at which the layers will partly integrate with each other and a continuous structure is achieved. By making a foam with different portions according to the above, i.e. a foam having a stepwise or continuous increasing particle concentration from one region thereof to another, it is possible to control the absorption properties so that an integrated structure is obtained which has a rapid liquid acquisition, good liquid distribution as well as storage capacity.

The invention therefore provides a method for making a foam material as described herein, said method comprising the steps of:

a. providing an partly or fully exfoliated dispersion of clay nanoparticles (C) in water;
b. adding one or more monomers which comprise neutral functional groups (B1),
c. adding a plasticizer,
d. optionally, adding a viscosity control agent and/or surfactant,
e. adding a polymerization initiator,
f. foaming the mixture of clay nanoparticles (C), plasticizer and neutral monomers (B1),
g. polymerising the neutral monomers (B1) to form a neutral claylinked foam,
h. hydrolysing the neutral functional groups (B1) to charged functional groups (A1)

wherein steps a., b., c., d. and e. can take place in any order.

The foaming step preferably takes place by means of a blowing agent, but may take place by means of any of the methods described above.

The present invention also relates to fibres comprising a claylinked gel as described herein. One particular advantage of using claylinked fibers in absorbent articles includes the possibility to produce cellulose-free products. In addition, it is easy to produce a product which is soft, flexible, thin, elastic and underwear like, which provides products with improved fit and comfort. An elastic core composed of the fibers of the invention will give better dry and especially wet integrity. The elastic claylinked material has the potential to improve the elasticity and integrity of the core. Furthermore, less core material may be needed as compared to traditional absorbent cores. The present invention also makes it easy to place the absorbent material where it is needed (as the traditionally-used particulate superabsorbent material is more free to move).

The fibres may be present in a fibrous network, such as those commonly used in absorbent components of absorbent articles. The process of manufacturing fibres is called spinning. There are three main types of spinning: melt, dry, and wet. Melt spinning is used for polymers that can easily be melted. Dry spinning involves dissolving the polymer into a solution that can be evaporated. Wet spinning is used when the solvent cannot be evaporated and must be removed by chemical means. All types of spinning use the same principle. In melt spinning, a mass of polymer is heated until it will flow. The molten polymer is pumped to the face of a metal disk containing many small holes, called the spinneret. Tiny streams of polymer that emerge from these holes (called monofilaments) are solidified as they cool down. The filaments are also wound together as they solidify, forming a long fibre. Wet spinning is used for fibre-forming substances that have been dissolved in a solvent. The spinnerets are submerged in a chemical bath and as the filaments emerge they precipitate from solution and solidify. Dry spinning is also used for fiber-forming substances in solution. However, instead of precipitating the polymer by solution or chemical reaction, solidification is achieved by evaporating the solvent in a stream of air or inert gas.

Gel spinning is a special process of dry and wet spinning used to obtain high strength or other special fibre properties. The polymer is not in a true liquid state during extrusion. Not completely separated, as they would be in a true solution, the polymer chains are bound together at various points in liquid crystal form or by other physical interactions. This produces strong inter-chain forces in the resulting filaments that can significantly increase the tensile strength of the fibres. In addition, the liquid crystals or other physical interactions are aligned along the fibre axis by the shear forces during extrusion. The filaments emerge with an unusually high degree of orientation relative to each other, further enhancing strength.

New spinning techniques include electrospinning. Electrospinning uses an electrical charge to draw very fine (typically on the micro or nano scale) fibres from a liquid. Electrospinning shares characteristics of both electrospraying and conventional wet spinning of fibres. Preferred spinning methods are wet and dry spinning and electrospinning.

Following the spinning process, the extruded fibres solidify. In some cases even after they have hardened the fibres can be stretched substantially—to produce increased chain alignment in order to yield improved strength.

The invention therefore provides a method for making a fibre as described herein, comprising the steps of:
a. providing an partly or fully exfoliated dispersion of clay nanoparticles (C) in water;
b. adding one or more monomers which comprise neutral functional groups (B1),
c. adding a plasticizer,
d. adding a polymerization initiator,
e. polymerising the monomer to form a neutral claylinked gel (B),
f. spinning the charged claylinked gel (A) into a fibre
g. hydrolysing the neutral functional groups (B1) to charged functional groups (A1), thus forming a charged claylinked gel (A),
wherein steps a., b., c. and d. and f. and g. can independently take place in any order.

The present invention also relates to film comprising a claylinked gel as described herein. In addition to the advantages listed above for fibres, films according to the invention allow the possibility to design superabsorbent laminates. Superabsorbent particles could be incorporated in the film or superabsorbent particles could be placed in between two films (sandwich structure). Furthermore, films make it easy to design an anatomically shaped core. In addition, the opportunity exists to introduce absorption capacity in new places in the diaper, e.g. in an absorbent standing gather or in the waist region to prevent leakage.

Polymeric films can be produced through several commercial known techniques like film blowing, film extrusion, film casting and film calendering. For films based on claylinked gels, calendering and extrusion are preferred methods.

In calendering the film, the thick semisolid gel may be fed through the calendering train in a single or a multiple passes through the calendering nips. The rolls or nips are maintained at temperatures suitable for the polymer gel including the solvent and the rolls or nips the temperature could be adjusted to evaporate the solvent (for instance water).

In film extrusion the thick semisolid gel may be fed into the extruder comes into contact with a screw. The rotating screw forces the gel forward into a barrel which could be heated to an appropriate temperature. In most processes, a heating profile is set for the barrel which ends at the outlet, the die. The die gives the final product its shape and after the die the temperature could be adjusted to evaporate the solvent (for instance water).

The invention therefore provides a method for making a film as described herein, comprising the steps of:
a. providing an partly or fully exfoliated dispersion of clay nanoparticles (C) in water;
b. adding one or more monomers which comprise neutral functional groups (B1),
c. adding a plasticizer,
d. adding a polymerisation initiator,
e. polymerising the neutral monomers (B1) to form a neutral claylinked gel,
f. forming the neutral claylinked gel into a film,
g. hydrolysing the neutral functional groups (B1) to charged functional groups (A1)
wherein steps a., b., c. and d. and steps f. and g. can take place in any order.

The foams, films and fibres of the present invention comprise a plasticizer. By plasticising agent/plasticizer is meant a chemical substance that is used together with a polymeric material to change its mechanical properties from hard and stiff to soft and flexible. Plasticising agent/plasticizers embed themselves in between the polymer chains, spacing them apart thereby increasing the free volume, and thus significantly lowering the glass transition temperature of the polymer and making it softer.

Water will act as a plasticising agent/plasticizer together with claylinked charged gel. However, water is not considered a plasticising agent/plasticizer in the present application since the function of absorbent products is to absorb water solutions. Relying on water as a plasticising agent/plasticizer will impair the function of the product. Other parameters that hinder the use of water as a plasticising agent/plasticizer: potential microbial growth could aggravate and difficulty to ensure constant water content.

Plasticizing agents selected for use in the present invention possess a range of properties. Generally, the plasticizing agents can be liquid or a solid and have a range of molecular weights and architectures and are compatible with the charged claylinked gel. They could be low molecular weights substances or polymers and are non-volatile and non-reactive.

Generally, liquid plasticizing agents are chosen to be miscible with the monomers which are used in the polymerization. Additionally, the plasticizing agents can have a range of molecular weights and architectures. That is, the plasticizing agents can be either a low molecular weight substance or a polymer. Typically, low molecular weight plasticizing agents are derived from low molecular weight acids or alcohols; examples are glycerol and citric acid. The low molecular weight acids or alcohols could also be esterified with respectively a monofunctional alcohol or monofunctional acid. Examples of such plasticising agents are esters of mono- and multibasic acids, such as isopropyl myristate, dibutyl phthalate, diisoctyl phthalate, dibutyl adipate, dibutylsebacate and the like. Typically polymeric plasticizing agents include polyalkylene oxides having weight average molecular weights of about 150 to about 1500, such as polyethylene oxides, polypropylene oxides, polyethylene glycols and copolymers thereof.

Useful plasticizing agents are compatible with the charged claylinked gel, such that once the plasticizing agent is mixed with the reaction mixture, the plasticizing agent does not phase separate. Some migration of the plasticizing agent from or throughout the charged claylinked gel can be tolerated, such as minor separation due to composition equilibrium or temperature influences, but the plasticizing agent does not migrate to the extent of phase separation between the charged claylinked gel and the plasticizing agent. When polymeric plasticizing agents are used, they tend to be a bit more limited in their applications than low molecular weight plasticizing agents and, in general, the lower the molecular weight of the polymeric plasticizing agent, the higher their compatibility with the charged claylinked gel.

Plasticizing agents used in the present invention are also non-volatile. If the plasticizing agent is to be used in the polymerization process where the claylinked gel is formed in the presence of the plasticizing agent, then the plasticizing agent not only solvates the monomers, but also remains present and stable during polymerization. Additionally, useful plasticizing agents are non-reactive, thus preventing copolymerization with the other monomers present in the polymerization process.

Additionally, to increase the foam stability the foams according to the invention may comprise one or more viscosity control agents which serve to increase the viscosity of the reaction mixture. Examples of viscosity control agents are synthetic hydrophilic polymers, polymers such as polyvinylalcohols or polyacrylic acid, or various cellulose derivatives such as carboxymethyl cellulose, hydroxyethyl cellulose, ethyl hydroxyethyl cellulose or hydrophobically modified ethyl hydroxyethyl cellulose (Bermocoll).

To increase foamability and the foam stability of the mixture during manufacture, foams according to the invention may comprise one or more surfactants.

Surfactants or surface active agents are characterized by its tendency to absorb at surfaces and interfaces. The term interface denotes a boundary between any two immiscible phases whereas the term surface indicates that one of the phases is a gas. Surfactants are wetting agents that lower the surface tension of a liquid or lower the interfacial tension between two liquids. Surfactants are usually organic compounds that are amphiphilic meaning they contain both hydrophobic groups and hydrophilic groups. A surfactant facilitates the formation of a foam and/or enhances its colloidal stability by inhibiting the coalescence of bubbles.

The foams, films and fibres of the present invention also comprise a charged claylinked gel (A). The charged claylinked gel (A) comprises clay nanoparticles (C) which are crosslinked by a charged polymer (A') such that any particular clay nanoparticle is linked to at least one other clay nanoparticle by said charged polymer (A'). Alternatively, the charged claylinked gel (A) can be considered as charged polymer (A') which is crosslinked by clay nanoparticles (C).

Suitably, the charged polymer (A') is polyacrylate or polyacrylsulfonate. A preferred charged polymer (A') is polyacrylate. As described above, the term "polyacrylate" is used to refer to a polymer which—at least in regions thereof—has a hydrocarbon backbone with pendant carboxylic acid and/or carboxylate groups. In that they are "pendant", the carboxylic acid/carboxylate groups are not part of the polymer backbone. Counterions for the polyacrylate may be any suitable positively-charged ions, such as e.g. $Na^+$, $K^+$ or $NH_4^+$. Other monomers may also be present in the polyacrylate, but it is preferable for liquid absorption properties that the majority of the polyacrylate (e.g. 50-100 wt. %) comprises acrylate/acrylic acid monomer.

The clay nanoparticles (C) in the claylinked gels may be selected from the group consisting of: montmorillonite, saponite, nontronite, laponite, beidellite, iron-saponite, hectorite, fluorohectorite, sauconite, stevensite, magdite, vermiculite, kaolin minerals (including kaolinite, dickite and nacrite), mica minerals (including illite), chlorite minerals, palygorskite, and combinations thereof. Preferred clay nanoparticles are montmorillonite, laponite and hectorite.

The clay nanoparticles typically have an average particle diameter of 5-500 nm, preferably 5-100 nm, more preferably 5-50 nm.

In that the claylinked gels are charged, i.e. they comprise a charged polymer (A'), they exhibit better absorption properties (higher absorption rate and higher absorption capacity) the neutral claylinked gels (B) which comprise neutral polymers (B'). This is evidenced in the experimental section and—in particularly—in FIG. 4.

A method is also provided for producing a charged claylinked gel (A). The charged claylinked gel (A) comprises clay nanoparticles which are crosslinked by a charged polymer (A') comprising charged functional groups (A1).

The method involves subjecting a neutral claylinked gel (B) comprising partly or fully exfoliated clay nanoparticles which are crosslinked by a neutral polymer (B') comprising neutral functional groups (B1) to hydrolysis, such that at least a portion of the neutral functional groups (B1) in the neutral polymer (B') are hydrolysed to charged functional groups (A1). At least 10 mol %, such as at least 30 mol %, or at least 40 mol % of the neutral functional groups (B1) in the neutral polymer (B') are hydrolysed to charged functional groups (A1).

The clay nanoparticles should be exfoliated since this will give a stable dispersion and a more homogenous gel. This has been shown to be an important factor in producing elastic and strong claylinked gels.

The neutral claylinked gels (B) from which the charged claylinked gels are produced can be manufactured by for example the method described for polyacrylamides in EP 1 160 286; i.e. providing an aqueous dispersion of clay nanoparticles at a suitable pH and temperature, adding the monomer of the neutral polymer (B') and initiator system, polymerising the monomer and purifying/isolating the neutral claylinked gels (B). Monomers of the neutral polymer (B') are selected according to the desired neutral polymer (B'), although acrylamide and acrylic ester monomers are most suitable.

The polymerisation reaction used to produce the neutral claylinked gels (B) includes polymerisation initiators and/or polymerisation catalysts. Example of initiators known in the art are peroxides (e.g. benzoyl peroxide) and azo compounds. Examples of catalysts include N,N',N'-tetramethylethylenediamine (TEMED) and β-dimethylaminopropionitrile. Irradiation by UV light also initiates polymerisation reactions. Preferred polymerisation initiators and catalysts, when making the foam materials, are redox initiators, which initiate polymerisation through the occurrence of one-electron transfer steps to form free radical intermediates, e.g. potassium persulfate and TEMED. When using said redox initiator the first initiator is added as in the method for making the foams according to the present invention and the second initiator/catalyst is added between step f. and g., i.e. just before polymerising the neutral monomers (B1) to form neutral foam.

The preferred solvent for the polymerisation reaction is water. However, other solvents such as alcohols, ethers or amide solvents (e.g. DMF) may be used, alone or in combination with water. The polymerisation reaction can take place at a temperature between −40° C. and 100° C., and the reaction temperature can be used to control the reaction rate (polymerisation reactions are generally exothermic).

A preferred weight ratio of neutral polymer (B') to clay nanoparticles (C) lies within the range 0.01 to 10, preferably between 0.03 and 4, most preferably between 0.1 and 4.

The use of organic bulk cross-linking agents in the neutral claylinked gel (B) can be reduced, as good cross-linking can be obtained via the clay nanoparticles. However, organic bulk cross-linking agents may be included in the polymerisation reaction so as to obtain desired gel strength and liquid absorption properties in the neutral claylinked gel (B). Organic bulk cross-linking agents are compounds having more than one (e.g. 2) polymerisable functional groups which can be incorporated into a growing neutral polymer in the polymerisation reaction. They act to bridge polymer chains, providing strength to the resultant gel. Known cross-linking agents are e.g. triallylisocyanurate, triallylcyanurate, N,N'-bisacrylylcystamine, N,N'-diallyltartardiamide, 1,3-diacryloylethyleneurea, ethylenediacrylate, N,N'-methylenebisacrylamide, N,N'-propylenebisacrylamide, di(acrylamindemethyl)ether, 1,2-diacrylamide ethyleneglycol and 1,3-diacryloylethyleneurea.

Although the gels may exclude organic bulk cross-linking agents, optionally surface cross-linking agents may be included which link the surfaces of claylinked foam, fibres and films. Once the neutral claylinked gel (B) is formed, the neutral functional groups (B1) are transformed into charged functional groups (A1), thus providing charged claylinked gel (A).

FIG. 1 illustrates possible synthesis routes for making charged (carboxylic acid) functional groups (A1) from a variety of neutral functional groups (B1). It shows that carboxylic acid groups can be synthesised by hydrolysis from nitrile (—CN), acid halide (—COX, where X=I, Br, Cl or F), ester (—CO$_2$R, in which R is a hydrocarbon), lactone (cyclic ester), anhydride (—CO—O—CO—) and amide (—CONH$_2$) groups. All of the neutral functional groups (B1) shown in FIG. 1 can be transformed to carboxylic acid functional groups by hydrolysis.

Monomers which comprise the neutral functional groups (B1) listed in FIG. 1 are known. Neutral claylinked gels (B) are formed from such monomers, as per EP 1 160 286. Hydrolysis of such neutral claylinked gels (B) provides charged claylinked gels, according to the method of the invention.

For example, acrylonitrile (CAS 107-13-1) can be polymerised in the presence of clay nanoparticles to provide poly(acrylonitrile) claylinked gel. Hydrolysis of the nitrile group of the poly(acrylonitrile) polymer gives polyacrylate claylinked gel.

Similarly, acryloylchloride (CAS 814-68-6) can be polymerised in the presence of clay nanoparticles using standard polymerisation techniques to provide poly(acryloylchloride) claylinked gel. Hydrolysis of the acid chloride of the polymer gives polyacrylate claylinked gel.

Acrylic esters (e.g. tert-butyl- or methylacrylic acid ester) can be polymerised in the presence of clay nanoparticles to provide poly(acrylic ester) claylinked gel. Hydrolysis of the ester group of the polymer gives polyacrylate claylinked gel. Colloid and Polymer Science, Vol., 272, no. 4 (1994) describes the hydrolysis of non-claylinked polyacrylic ester gels to polyacrylic acid gels. t-Butyl and methylacrylic acid esters are most favoured, as hydrolysis can be carried out under relatively mild conditions.

Lactones are cyclic esters, and unsaturated lactones can be polymerised in the presence of clay nanoparticles to provide claylinked gels comprising polymers with pendant lactone groups (see e.g. U.S. Pat. No. 6,534,239). Hydrolysis of the lactone group of the polymer gives polyacrylate claylinked gel.

Anhydrides contain the neutral functional group (—CO—O—CO—). Anhydrides containing an unsaturated moiety can be polymerised in the presence of clay nanoparticles to provide claylinked gels with polymers with pendant anhydride groups (e.g. polymerisation of itaconic anhydride, see Polymer, 2005, 50, no. 2 or Polymer Bulletin 32, 169-172, 1994). Additionally, polymers with pendant anhydride groups can be made by irradiation of maleic anhydride (see Macromolecules, vo. 31, no. 13, 1998). Hydrolysis of the anhydride group of the polymer gives polyacrylate claylinked gel.

Polymers containing amide (—CONH$_2$) groups are known, as are their claylinked gels (e.g. polyacrylamide and polyacrylamide claylinked gel in EP 1 160 286). Hydrolysis of the amide group in such gels gives polyacrylate claylinked gel. Of the above neutral functional groups (B1), amide groups are preferred.

As described above, the term "polyacrylamide" is used to refer to a polymer which—at least in regions thereof—has a hydrocarbon backbone with pendant amide groups. In that they are "pendant", the amide groups are not part of the polymer backbone. The presence of amide linkages in the backbone is undesirable, as hydrolysis conditions may cause fragmentation of the polymer chains themselves. Preferably, the polyacrylamide comprises or consists of monomers having at least one polymerisable alkene group and at least one amide group. Suitably, the monomers comprising the polyacrylamide have only one polymerisable alkene group, to avoid excessive cross-linking between polyacrylamide chains. More preferably, the polyacrylamide is derived from acrylamide monomer (CH$_2$=CHCONH$_2$). Other monomers may also be used, such as secondary (CH$_2$=CHCONHR) or tertiary (CH$_2$=CHCONR'R) acrylamides, or other alkenes, but it is preferable for liquid absorption properties that the majority of the polyacrylamide (e.g. 50-100 wt. %) is derived from acrylamide monomer.

Figure 2:
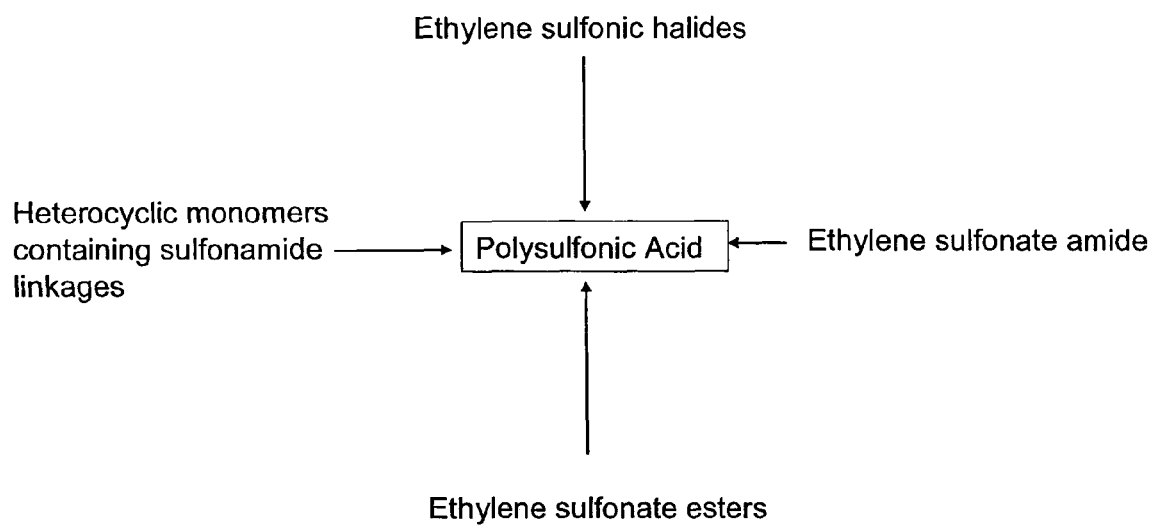
FIG. 2 is an illustration of synthesis routes for making sulfonic acid functionalities.

FIG. 2 illustrates possible synthesis routes to polysulfonic acid. Polysulfonic acid refers to a polymer which—in at least regions thereof—has a hydrocarbon backbone with pendant sulfonic acid or sulfonate groups. In that they are "pendant", the sulfonate/sulfonic acid groups are not part of the polymer backbone. Preferably, the polysulfonic acid comprises or consists of monomers having at least one polymerisable alkene (olefin) group and at least one sulfonate or sulfonic acid group. Suitably, the monomers comprising the polysulfonic acid have only one polymerisable alkene group, to avoid excessive cross-linking between polysulfonic acid chains. More preferably, the polysulfonic acid comprises or consists of pendant sulfonate (—SO$_3^-$) and/or sulfonic acid (—SO$_3$H) groups. Other functional groups may also be present, such as other alkenes, but it is preferable for liquid absorption properties that the majority of the polysulfonic acid (e.g. 50-100 wt. %) comprises pendant sulfonate or sulfonic acid groups.

Charged claylinked gels comprising polysulfonic acid can be synthesised by first polymerising ethylene sulfonate amide in a dispersion of clay nanoparticles to provide the corresponding neutral claylinked gel. This gel can then be hydrolysed to provide polysulfonic acid claylinked gel.

Similarly, ethylene sulfonate esters, ethylene sulfonic halides and heterocyclic monomers containing sulphonamide linkages can be polymerised in the presence of a dispersion of clay nanoparticles to provide neutral claylinked gels. These gels can be hydrolysed to provide polysulfonic acid claylinked gels.

The gel has been described with reference to a range of neutral monomers. Combination of these monomers with each other, and with other monomers, is possible when forming the neutral polymers according to the invention.

Suitably, in the method described herein for producing charged claylinked gel (A), the charged claylinked gel (A) is polyacrylate claylinked gel; the charged polymer (A') is polyacrylate; the charged functional groups (A1) are carboxylic acid groups and the neutral functional groups (B1) are selected from the group comprising: amide, nitrile, anhydride, lactone, acid halide and ester, preferably amide.

Hydrolysis of polyacrylamide gels to polyacrylic acid gels may be carried out using aqueous acidic solution, see G. Smets, A. M. Hesbain, J. Polymer Science., Vol. 11, p. 217-226 (1959).

Alternatively, hydrolysis of the neutral claylinked gel (B) to the charged claylinked gel (A) is carried out by exposing the neutral claylinked gel (B) to an elevated pH, i.e. above pH 8. This may be carried out by using aqueous basic solutions comprising salts of the metals of groups I and II of the periodic table. An example of a suitable basic solution is sodium acetate. The basic aqueous solution preferably has a pH of above 8.

In that hydrolysis is the cleavage of a functional group with water, water is an essential component of the hydrolysis reaction. However, it need not be the only solvent, and successful hydrolysis reactions can take place in the presence of co-solvents such alcohols, DMF, and ethers which improve the solubility of organic components in the reaction mixture.

The hydrolysis reaction is suitably carried out at a temperature between 45 and 95, preferably between 60 and 80° C. The reaction temperature can be used to control the reaction rate.

Through the method described herein, the difficulties involved in adding charged components to dispersions of clay nanoparticles can be avoided, as crosslinking is carried out using a neutral polymer (B'). Once they have been crosslinked by the neutral polymer (B), the clay nanoparticles are stable (e.g. do not aggregate) under hydrolysis conditions.

An article by Zhang et al. in *Journal of Polymer Science; Part A: Polymer Chemistry, Vol.* 44 (2006), 6640-6645 describes how post-treatment of nanocomposite (i.e claylinked) polyacrylamide hydrogels at 40° C. provides a hydrogel with high mechanical strength and high swelling ratio. It is concluded that the chemical components of the gel (i.e. polyacrylamides) do not change under a 20-day post-treatment at 40° C.

A charged claylinked gel (A) is obtainable through the method described herein, in particular a polyacrylate claylinked gel.

The present invention further relates to the use of a foam, film or fibre according to the invention in an absorbent article, and an absorbent article comprising the foam, film or fibre according to the invention. Absorbent articles include diapers, incontinence guards, sanitary napkins, panty liners, bed protectors and the like. They are preferably disposable, i.e. are intended for single use. Typically, absorbent articles comprise a liquid-permeable topsheet, a liquid-impermeable backsheet and an absorbent core. The topsheet and backsheet generally have a similar extension in the plane of the article, while the absorbent core has an extension which is somewhat smaller. The topsheet and backsheet are joined to one another around the periphery of the absorbent core, so that the core is enclosed within the envelope formed by the topsheet and the backsheet. The absorbent core is at least located in the crotch portion of the article, and may also extend somewhat into the front and rear portions. The topsheet and backsheet may be joined to one another by any means common in the art, e.g. ultrasonic welding, thermal welding or gluing.

The absorbent core of the article acts to receive and contain liquid and other bodily exudates. As such, it may contain the foam, film or fibre according to the present invention, and may contain additional absorbent materials. Examples of commonly-occurring absorbent materials are cellulosic fluff pulp, tissue layers, highly-absorbent polymers (so called superabsorbents), absorbent foam materials, absorbent non-woven materials or the like. It is common to combine cellulosic fluff pulp with superabsorbents in an absorbent body. It is also common to have absorbent cores comprising layers of different material with different properties with respect to liquid receiving capacity, liquid distribution capacity and storage capacity. The thin absorbent cores, which are common in for example baby diapers and incontinence guards, often comprise a compressed mixed or layered structure of cellulosic fluff pulp and superabsorbent. The size and absorbent capacity of the absorbent core may be varied to be suited for different uses such as for infants or for incontinent adults.

The absorbent core may comprise one or more layers which are designed to improve the handling of bodily waste. Such layers are designed to receive a large amount of liquid in a short space of time and distribute it evenly across the absorbent core. They may include so-called transfer, distribution, surge or acquisition layers; these layers are herein seen as being included in the absorbent core. The foam, film or fibre of the present invention may be present in one or more such layers, and even in all layers. The absorbent core may consists of the foam, film or fibre according to the invention, i.e. an absorbent core free of cellulose would be provided.

The charged claylinked gel (A) allows the formation of foams, films or fibres (particularly foams) in a controlled manner, which also affects the swelling of the gel in a controlled manner. It may be combined with other materials, especially other absorbent materials. In particular, it may be combined with fibrous materials, e.g. cellulosic fibres. It may be mixed with the fibres and/or applied as a layer between fibrous layers. It may be used as the sole superabsorbent material, or used in combination with other superabsorbent materials. The foam, film or fibre may be applied in localised areas of an absorbent core, e.g. in intake regions, liquid distribution regions and/or liquid retention regions.

The foam, film or fibre may be anchored to one or more components of the absorbent article in order to utilize the elasticity of the foam, film or fibre and thus providing an elastic absorbent article. Said component may be the topsheet, backsheet, the transfer, distribution, surge or acquisition layer or other components of the absorbent core.

The concentration of charged claylinked gel (A) in an absorbent core may be the same as that of conventional superabsorbent materials, e.g. from 2-100% inclusive, from 10-70% inclusive, e.g. from 20-60% inclusive, or from 30-50% inclusive of the total weight of the absorbent core (w/w). The person skilled in the art will understand how the concentration of charged claylinked gel in an absorbent article may be adjusted depending on the absorbent properties and the type of absorbent article which is to be produced, e.g. high amount of superabsorbent material may be used in order to achieve a thin absorbent article or to save material, while lower amounts may be used in some feminine hygiene articles.

The present invention further relates to the use of a foam, film or fiber according to the invention in an elastic absorbent article. When used in an elastic absorbent article said foam, film or fiber is anchored to specific sites in order to use the elasticity of the foam, film or fiber and to achieve an elastic absorbent article.

Detailed methods for making the fibres, films and foams of the invention are provided in the following Examples.

The present invention should not be considered as limited by the above embodiments and the Figures, but rather the scope of protection should be determined by the enclosed claims. Combinations of features and elements as described for various embodiments above should also fall within the scope of the invention.

Example 1

Clay-Linked Gels

Materials

Acrylamide, Laponite XLS, N,N,N',N'-tetramethyldiamine (TEMED), potassium persulfate (KPS) and sodium acetate trihydrate were used as received. Deionised water was also used in the experiments.

Methods

Laponite XLS (13.5 g) was exfoliated in deionised water (150 g) in an Erlenmeyer flask using magnetic stirring for about 30 minutes. Acryl amide (15 g) was dissolved in the transparent exfoliated dispersion under an inert atmosphere at room temperature. TEMED (120 µl) and finally an aqueous solution of KPS (7.5 ml, 2 w/w %) was added to the dispersion before it was transferred into glass tubes and allowed to polymerize at 30° C. for 24 hours.

Two gels were transferred into cans and covered with an aqueous solution of sodium acetate (1 w/w %) before the cans were capped and put in an oven at 80° C. for about 24 hours and 96 hours, respectively. A third gel was stored in room temperature for 16 hours. All gels were washed in a large excess of deionised water for at least three days and the water was changed three times during this period. The gels were dried in an oven at 40° C. before they were milled.

Figure 3:
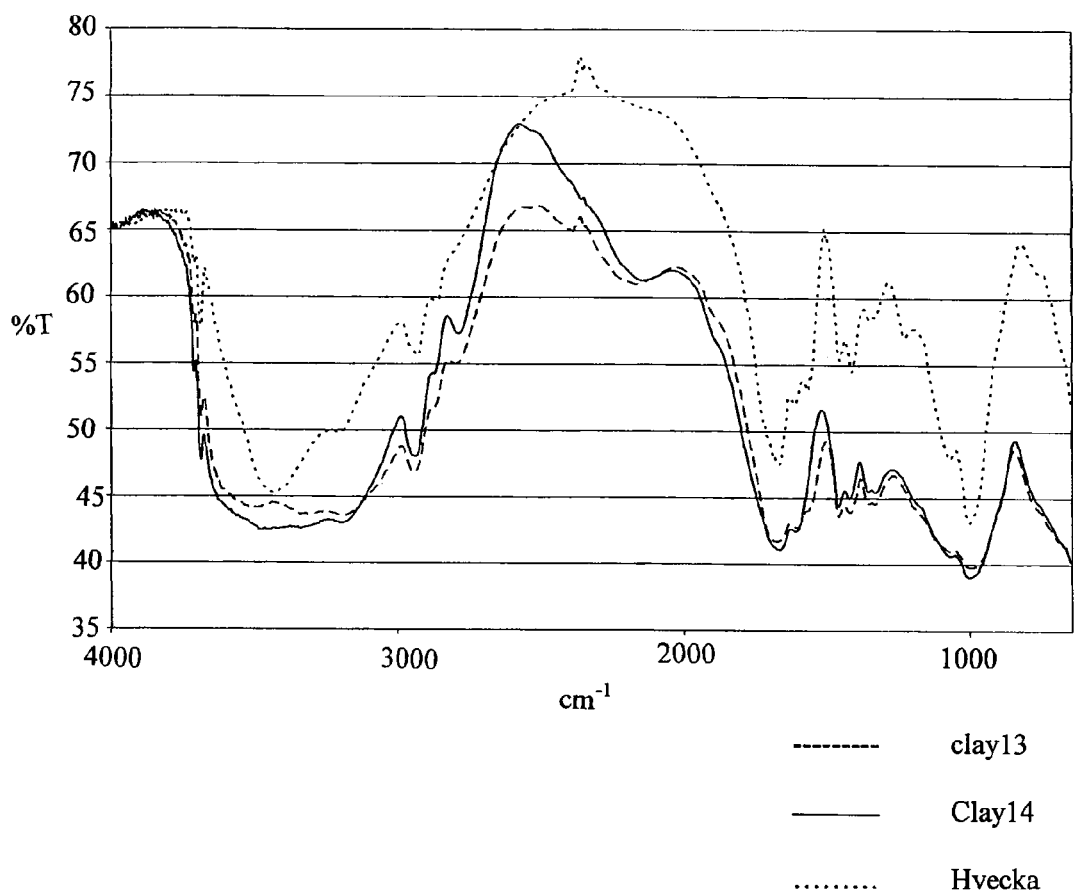
FIG. 3 shows FTIR spectra of claylinked gels.

The produced gels were characterized regarding their chemical composition using FTIR and regarding their swelling capacity using Edana test methods 440.1-99 (Absorbency I). The FTIR analysis was performed as transmission analysis of KBr tablets composed of 0.01 g sample and 0.20 g KBr and the combined IR spectra of each gel is shown in FIG. 3.

Results

Chemical Composition

The amide-group in polyacrylamide is partly hydrolyzed to a carboxylate anion-group. This is visible in the carbonyl region in the FTIR spectra.

The continuous line (clay 14) is the reference (polyacrylamide claylinked gel not submitted to hydrolysis). The dashed graph (clay 13) is polyacrylamide claylinked gel submitted to sodium acetate and heat for 24 hours. The dotted graph (Hvecka) is polyacrylamide claylinked gel submitted to sodium acetate and heat for 96 hours.

In the reference spectra two peaks are localized in carbonyl region; at 1666 cm$^{-1}$ and 1603 cm$^{-1}$ respectively. A third peak in the carbonyl region at 1553 cm$^{-1}$ is visible for the hydrolyzed gels. It is first visible as a shoulder for the sample that is hydrolyzed for 24 hours and as a distinct peak for the sample that is hydrolyzed for 96 hours. The growth of this peak at 1553 cm$^{-1}$ is related to the increase of carboxylate anion groups.

Figure 4:
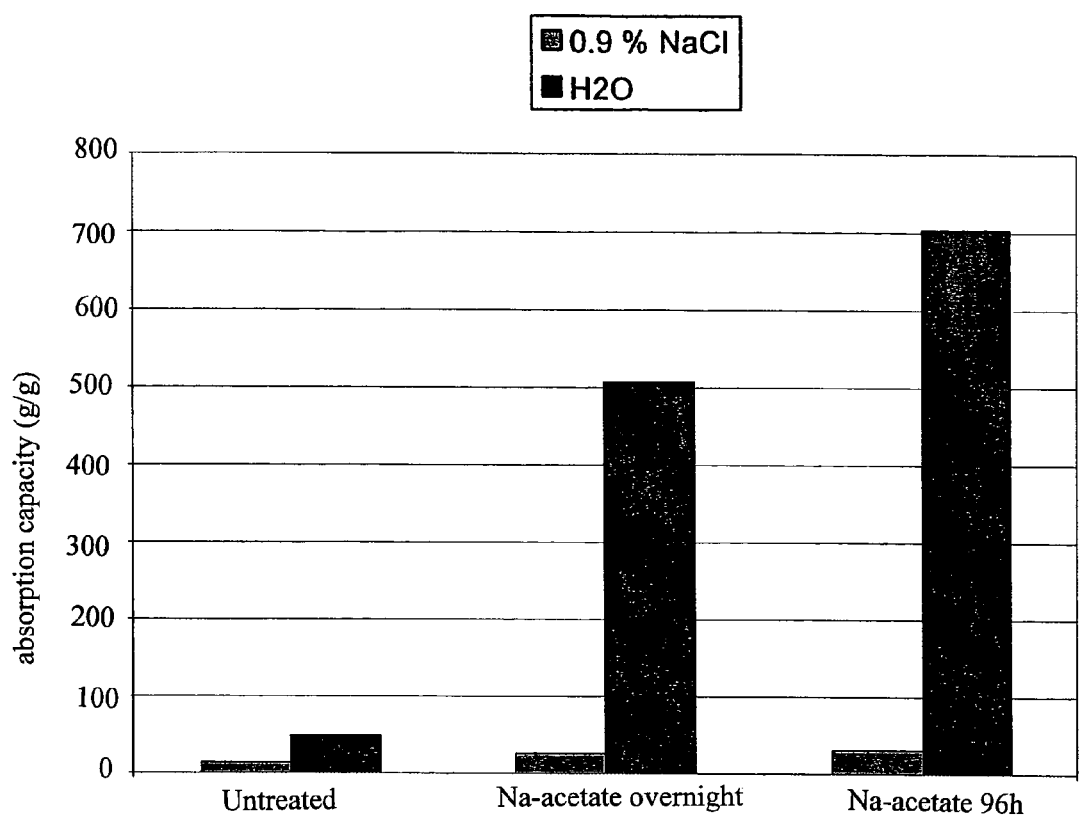
FIG. 4 shows the Free swelling (g/g) of claylinked gels.

The change in chemical composition is accompanied by an increase of the swelling capacity according to FIG. 4, which shows the Absorption Capacity (g/g) of untreated polyacrylamide claylinked gel, polyacrylamide claylinked gel treated with sodium acetate solution as described above for 24 hours and polyacrylamide claylinked gel treated with sodium acetate solution as described above for 96 hours. Values are provided for absorption capacity for both 0.9% w/w NaCl solution and distilled water (H$_2$O). It can be seen that the Absorption Capacity of polyacrylamide claylinked gel treated with sodium acetate solution increases substantially, as amide groups are hydrolysed to free carboxylic/carboxylate groups.

Example 2

Freeze Dried Foam Based on Clay-Linked Polyacrylamide Gel

Preparation

Recipe 102.6 g ultrapure water produced in a Elga Maxima HPLC
7.5 g Laponite XLS, supplied by Rockwood Clay Additives
10.0 g glycerol, 98% from VWR International AB
7.5 g acrylamide, >99% from Merck
7.5 ml of a potassium persulfate solution composed of 2% (w/w) Potassium persulfate in ultrapure water. Potassiumsulfate from Merck
140 µl TEMED (N,N,N',N'-Tetramethylethylenediamine)>99% from Fluka
1.2 g Dermocoll EHM100 (EHEC) from Akzo Nobel Dermocoll is used as a viscosity control agent and is soluble in 85° C. ultrapure water. Dermocoll is dispersed in 30 ml hot (85° C.) ultrapure water and stirred for 15 min using a magnetic stirrer. 10 ml cold ultrapure water is added and stirred for additional 10 min.

The Laponite powder was carefully exfoliated into 102.6 g ultrapure water under stirring for 30 min using a 250 ml beaker and a magnetic stirrer. The beaker was cooled down using an ice-water bath. The acrylamide was added and when the acrylamide was dissolved, the glycerol was added Subsequently the solution based on Dermocoll was added and the mixture was stirred for 15 min. Finally the potassium persulfate solution was added. The resulting mixture is transferred to a reaction vessel which is composed of a 500 ml beaker with a lid and inlet and outled for gas. A balloon stirrer is used for whipping the mixture. The reaction vessel has been subjected to a nitrogen flow to get an inert atmosphere before the mixture is added.

The stirring is started (1800-1900 rpm) and nitrogen is bubbled through the mixture for 15 min. Subsequently the gas is turn off and the stirrer is slowed down to 400 rpm and TEMED is added. The resulting mixture is stirred for additional 30 sek before the resulting foam is transferred to a flat vessel and solidified in an oven at 50° C. for 24 h and subsequently transferred into an freezer at −80° C. for 24 h. The frozen foam was put into a manual Hetosicc Freeze Dryer, type FD3 (ID 872154) from Heto Lab Equipment for 48 h.

Figure 5:
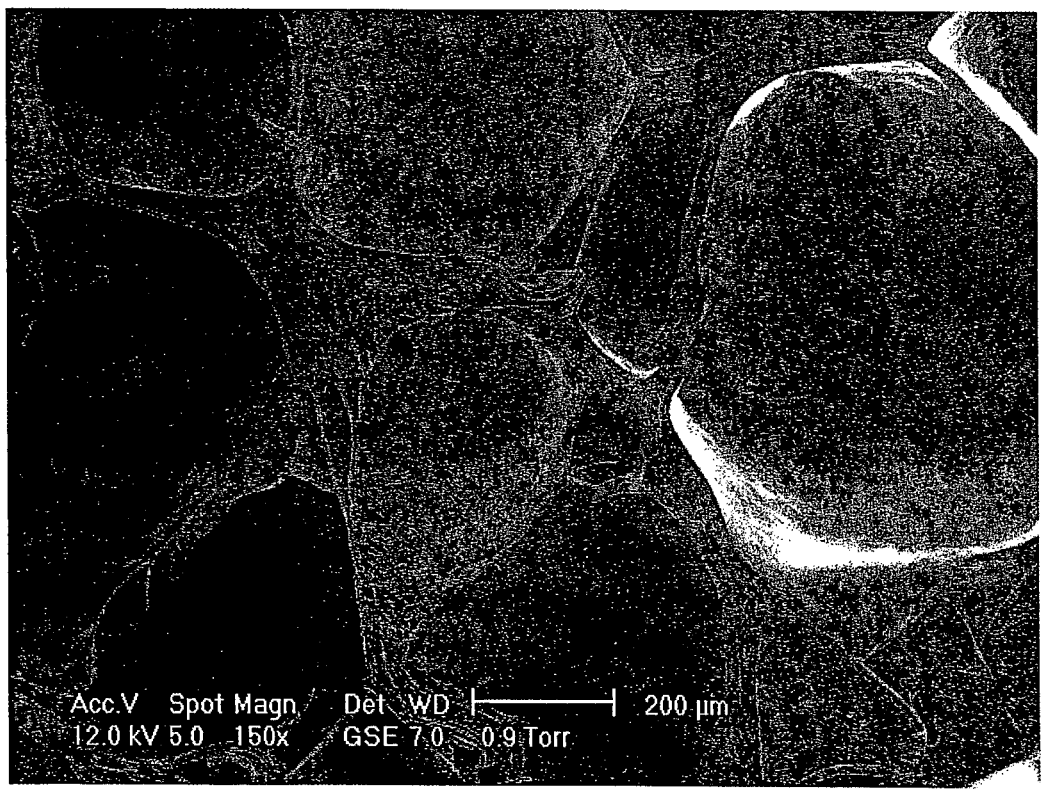
FIG. 5 is an E-SEM image of freeze-dried foam based on clay-linked polyacrylamide gel.

The resulting foam was analyzed using E-SEM and is shown in FIG. 5.

Example 3

Elastic Foams Based on Clay-Linked Polyacrylamide Gel

Recipe 102.6 g ultrapure water produced in a Elga Maxima HPLC
3 g, 12 g or 15 g respectively Laponite XLS, supplied by Rockwood Clay Additives The samples were denoted 2, 8 and 10% (w/w) Laponite respectively
20.0 g glycerol, 98% from VWR International AB
15.0 g acrylamide, >99% from Merck
7.5 ml of a potassium persulfate solution composed of 2% (w/w) Potassium persulfate in ultrapure water. Potassiumsulfate from Merck 140 μl TEMED (N,N,N',N'-Tetramethylethylenediamine)>99% from Fluka
1.2 g Dermocoll EHM100 (EHEC) from Akzo Nobel Dermocoll is used as a viscosity control agent and is soluble in 85° C. ultrapure water. Dermocoll is dispersed in 30 ml hot (85° C.) ultrapure water and stirred for 15 min using a magnetic stirrer. 10 ml cold ultrapure water is added and stirred for additional 10 min.

The Laponite powder was carefully exfoliated into 102.6 g ultrapure water under stirring for 30 min using a 250 ml beaker and a magnetic stirrer. The beaker was cooled down using an ice-water bath. The acrylamide was added and when the acrylamide was dissolved, the glycerol was added. Subsequently the solution based on Dermocoll was added and the mixture was stirred for 15 min. Finally the potassium persulfate solution was added. The resulting mixture is transferred to a reaction vessel which is composed of a 500 ml beaker with a lid and inlet and outlet for gas. A balloon stirrer is used for whipping the mixture. The reaction vessel has been subjected to a nitrogen flow to get an inert atmosphere before the mixture is added.

The stirring is started (1800-1900 rpm) and nitrogen is bubbled through the mixture for 15 min. Subsequently the gas is turned off and the stirrer is slowed down to 400 rpm and TEMED is added. The resulting mixture is stirred for additional 30 sec before the resulting foam is transferred to a flat vessel and put into an oven at 50° C. for 48 h.

Mechanical Analysis

The dried samples were stored at 23° C. and 50% RH for three days before mechanical analysis was performed.

Mechanical analysis was performed using a tensile tester (Lloyd LRX) The measurements were carried out at a constant crosshead speed of 100 mm/min using a 500 N load cell and a preload of 0.02N.

The foams were cut in pieces with the length of 80 mm. The width was 15 mm+/−1 mm and the thickness was in the region of 0.2-0.5 mm. A sliding caliper was used to measure said thickness in an uncompressed state. Each sample was analyzed individually.

A distance of 50 mm (which corresponds to the gauge length between the clamps) was marked on the samples. To ensure that the samples should not slip out of the clamps a tape was put on the samples exactly at the marks. The sample was then mounted into the clamps.

TABLE 1

Mechanical properties of elastic foams

| % (w/w) Laponite | Strain at yield (MPa) | Elongation at break (%) |
|---|---|---|
| 10 | 7.7 | 103 |
| 8 | 3.0 | 198 |
| 2 | 1.2 | 126 |

As can be seen from Table 1, it is possible to make foam materials which are elastic in the dry state by using an external plasticizing agent.

Example 4

Elastic Fibres Based on Clay-Linked Polyacrylamide Gels

Preparation of Clay-Linked Polyacrylamide Gel
112.4 g ultrapure water produced in an Elga Maxima HPLC
15 g Laponite XLS, supplied by Rockwood Clay Additives
30.0 g glycerol, 98% from VWR International AB
15.0 g acrylamide, >99% from Merck
7.5 ml of a potassium persulfate solution composed of 2% (w/w) Potassium persulfate in ultrapure water. Potassiumsulfate from Merck
120 μl TEMED (N,N,N',N'-Tetramethylethylenediamine)>99% from Fluke The Laponite was carefully exfoliated into the 112.4 g ultrapure water under stirring for 1 h. The glycerol was added and subsequently the acrylamide. When the acrylamide was dissolved the solution was put into an ultrasonic bath (Branson 5200) for 1 h. Subsequently the solution was cooled down to 10° C. using a water-ice bath and the potassium sulphate solution and TEMED were added. The solution was now filled into 10 ml plastic syringes, provided with an injection needle cut to a length of 15 mm and the polymerization took place when the syringes was put into a waterbath at 30° C. for 24 h.

Fiber Manufacturing

A small amount of gel was pressed out from the syringe and discarded before fiber manufacturing started.

A small amount of the gel was pressed out and wrapped around a metallic circular bar until the length of the fibre was 9 cm in a vertical and in a relaxed state. The resulting gel-fibre was stretched to 23.5 cm and immersed in ethanol (99.5%) for 1 hour and 30 minutes. The fibre was allowed to dry at room temperature for at least 11 hours before mechanical testing was performed.

Mechanical Testing

Figure 6:
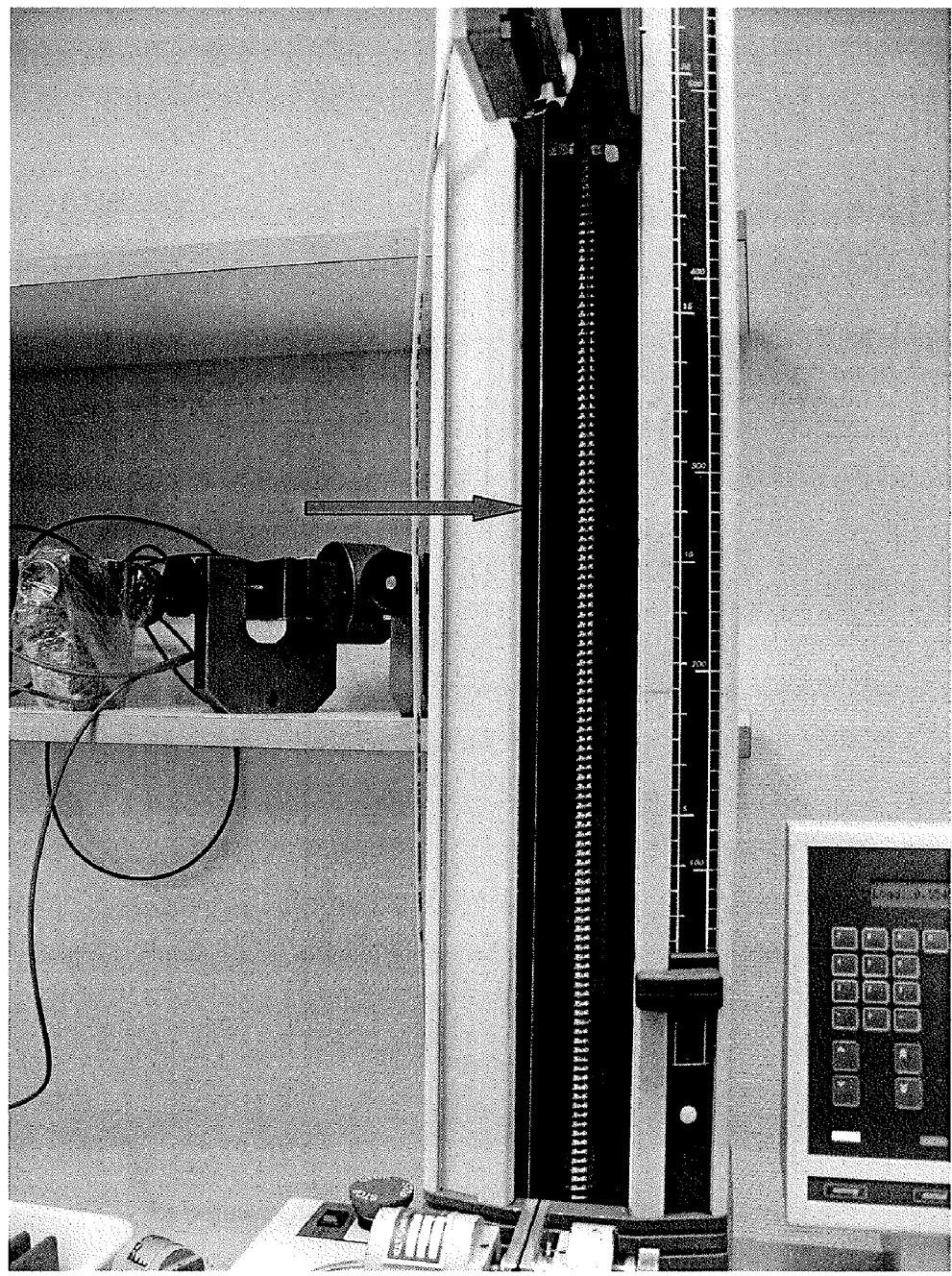
FIG. 6 shows fibres of clay-linked gel in the tensile tester.

The elongation at break was determined using a tensile tester (Lloyd LRX). The measurements were carried out at a constant crosshead speed of 500 mm/min using a 10 N load cell and a preload of 0.02N. The apparatus is shown in FIG. 6, and the arrow indicates the location of the fibre.

The fibres were cut in pieces with the length of 80 mm. A distance of 50 mm (which corresponds to the gauge length between the clamps) was marked on the fibres. A glass fibre reinforced tape (Tessla 25 mm×50 m from Westpack AB Sweden) was put on the threads exactly at the mark and before the tape was fastened the loose ends of the thread were stretched; the threads should not slide in the clamps or in the tape. The fibre was then mounted into the clamps very carefully to avoid stretching the fibre.

The fibre was extended until break and the load and the elongation at break are recorded in Table 2.

TABLE 2

Elastic property of fibres in dry state - four fibres produced as above were tested.

| Sample | Load at break (N) | Elongation at break (%) |
|---|---|---|
| 1 | 0.86 | 1060 |
| 2 | 0.87 | 1140 |
| 3 | 0.90 | 1114 |
| 4 | 0.84 | 1046 |

It can be seen that, by using a plasticizer, fibres which are very elastic in dry state could be produced.

The fibre was wetted in deionised water for 30 min. Subsequently the fibre was stretched manually. The fibre had an original length of 1 cm and it was easily stretched to a length of 8 cm without breaking. Thus, the elasticity was shown to be at least 700% of the original length. Consequently the clay-linked fibers remain elastic in wet condition. This test was performed manually compared to the test shown in table 2 and the full extension at break was not able to be recorded thereby the somewhat lower value.

Example 5

Elastic Film Based on Clay-Linked Polyacrylamide Gels

Preparation of Clay-Linked Polyacrylamide Gel
112.4 g ultrapure water produced in an Elga Maxima HPLC
15 g Laponite XLS, supplied by Rockwood Clay Additives
20.0 g glycerol, 98% from VWR International AB
15.0 g acrylamide, >99% from Merck
7.5 ml of a potassium persulfate solution composed of 2% (w/w) Potassium persulfate in ultrapure water. Potassiumsulfate from Merck
120 µl TEMED (N,N,N',N'-Tetramethylethylenediamine) >99% from Fluke The Laponite was carefully dispersed into the 112.4 g ultrapure water under stirring for 1 h. The glycerol was added and subsequently the acrylamide. When the acrylamide was dissolved the solution was put into an ultrasonic bath (Branson 5200) for 1 h. Subsequently the solution was cooled down to 10° C. using a water-ice bath and the potassium sulphate solution and TEMED were added.

Film Manufacturing

The gel was pressed out on silicone-coated paper. Another silicone-coated paper was placed on top of the gel and a rolling pin was used on the longitudinal direction of the gel to get a thinner sample. The paper with the gel was placed between two glass plates and the plates were pressed against each other and fixed with clamps on the four corners. After 48 hours the glass plates were removed and the sample was dried in a heating oven at 30 degree for 3 hours. The film was stored between the silicone coated papers until testing.

Mechanical Testing

The elongation at break was determined using a tensile tester (Lloyd LRX) The measurements were carried out at a constant crosshead speed of 500 mm/min using a 10 N load cell and a preload of 0.02N.

The films were cut in pieces with the length of 80 mm and width of 4 mm. A distance of 50 mm (which corresponds to the gauge length between the clamps) was marked on the films. A glass fibre reinforced tape (Tessla 25 mm×50 m from Westpack AB Sweden) was put on the threads exactly at the mark and before the tape was fastened the loose ends of the thread were stretched; the threads should not slide in the clamps or in the tape. The film was then mounted into the clamps very carefully to avoid stretching the film. The thickness of the film was 68 µm±3 µm. The thickness of the film was measured using a thickness gauge meter; Erichsen model 497, Measuring foot diameter=7 mm, Measuring pressure, 0.4 bar The film was extended until break and the load and the elongation at break are recorded in Table 3.

TABLE 3

Mechanical property of films - four films produced as above were tested.

| Sample | Load at break (N) | Elongation at break (%) |
|---|---|---|
| 1 | 1.86 | 594 |
| 2 | 1.05 | 612 |
| 3 | 1.72 | 726 |
| 4 | 1.59 | 588 |

As can be seen, highly elastic films based on claylinked gels could be produced.

The invention claimed is:

1. A fibre, film or foam comprising:
   a. a plasticizer and
   b. a charged claylinked gel, said charged claylinked gel comprising clay nanoparticles which are crosslinked by a charged polymer such that any particular one of the clay nanoparticles is linked to at least one another one of the clay nanoparticles by said charged polymer.

2. The fibre, film or foam according to claim 1, wherein the charged polymer is polyacrylate or polyacrylsulfonate.

3. The fibre, film or foam according to claim 2, wherein the polyacrylate comprises pendant carboxylate —($CO_2^-$)— or pendant carboxylic acid groups —($CO_2H$) and the polyacrylsulfonate comprises pendant sulfonate —($SO_3^-$) or pendant sulfonic acid groups —($SO_3H$).

4. The fibre, film or foam according to claim 1, wherein the clay nanoparticles are selected from the group consisting of montmorillonite, saponite, nontronite, laponite, beideilite, iron-saponite, hectorite, fluorohectorite, sauconite, stevensite, magdita, vermiculite, kaolin minerals, mica minerals, chlorite minerals, palygorskite, and combinations thereof.

5. The fibre, film or foam according to claim 1 wherein the clay nanoparticles have an average particle diameter of 5-500 nm.

6. The fibre, film or foam according to claim 1, in which wherein the charged polymer comprises less than 1 mol % of an organic bulk cross-linker, based on the content of charged monomer.

7. The fibre, film or foam according to claim 1, which is a foam.

8. The fibre, film or foam according to claim 7, wherein the foam has a pore size gradient from one region thereof to another.

9. The fibre, film or foam according to claim 7, wherein the foam has an increasing nanoparticle concentration from one region thereof to another.

10. The fibre, film or foam according to claim 7, further comprising at least one viscosity control agent.

11. A method for making a fibre, film or foam according to claim 7, comprising the steps of:
    a. providing a partly or fully exfoliated dispersion of clay nanoparticles in water;
    b. adding one or more monomers which comprise neutral functional groups,
    c. adding a plasticizer,
    d. optionally, adding a viscosity control agent or surfactant,
    e. adding a polymerisation initiator,
    f. foaming the mixture of the clay nanoparticles, the plasticizer and the neutral monomers,
    g. polymerising the neutral monomers to form a neutral claylinked foam,
    h. hydrolysing the neutral functional groups to charged functional groups,
    wherein steps a., b., c., d. and e. can take place in any order.

12. The method according to claim 11, wherein the foaming step takes place by means of a blowing agent.

13. The fibre, film or foam according to claim 1, which is a fibre.

14. A method for making a fibre according to claim 13, comprising the steps of:
    a. providing a partly or fully exfoliated dispersion of clay nanoparticles in water;
    b. adding one or more monomers, which comprise neutral functional groups,
    c. adding a plasticizer,
    d. adding a polymerization initiator, e. polymerising the monomer to form a neutral claylinked gel, f. spinning the charged claylinked gel into a fibre g. hydrolysing the neutral functional groups to charged functional groups, thus forming a charged claylinked gel, wherein steps a., b., c., and d and steps f. and g. may take place in any order.

15. The fibre, film or foam according to claim 1, which is a film.

16. A method for making a fibre, film or foam according to claim 15, comprising the steps of:

a. providing a partly or fully exfoliated dispersion of clay nanoparticles in water;

b. adding one or more monomers which comprise neutral functional groups, c. adding a plasticizer, d. adding a polymerisation initiator, e. polymerising the neutral monomers to form a neutral claylinked gel, f. forming the neutral claylinked gel into a film, g. hydrolysing the neutral functional groups to charged functional groups, wherein steps a., b., c. and d. and stops f. and g. can take place in any order.

17. An absorbent article comprising the foam, film or fibre according to claim 1.

18. The absorbent article according to claim 17, wherein said foam, film or fibre is anchored to one or more components of the absorbent article in order to utilize the elasticity of the foam, film or fibre.

19. An absorbent article comprising an absorbent core, said absorbent core consisting of the foam, film or fibre according to claim 1.

20. The fibre, film or foam according to claim 1, wherein the clay particles comprise montmorillonite, laponite or hectorite.

* * * * *